United States Patent [19]

Lin et al.

[11] Patent Number: 5,233,103
[45] Date of Patent: Aug. 3, 1993

[54] PREPARATION OF ORGANOALUMINUM COMPOUNDS AND LINEAR ALCOHOLS DERIVED THEREFROM

[75] Inventors: Ronny W. Lin; Robert H. Allen, both of Baton Rouge, La.; William L. Cox, Houston, Tex.

[73] Assignee: Ethyl Corporation, Richmond, Va.

[21] Appl. No.: 906,199

[22] Filed: Jun. 29, 1992

[51] Int. Cl.$^5$ .................. C07C 27/00; C07C 29/04
[52] U.S. Cl. ..................... 568/911; 568/840; 568/851; 568/810
[58] Field of Search ............... 568/840, 851, 886, 910, 568/911

[56] References Cited

U.S. PATENT DOCUMENTS

| | | | |
|---|---|---|---|
| 2,889,385 | 6/1959 | Catterall et al. | 260/683.15 |
| 2,959,607 | 11/1960 | Werber et al. | 260/448 |
| 2,962,513 | 11/1960 | Meiners et al. | 260/448 |
| 3,239,568 | 3/1966 | Pree et al. | 568/909.5 |
| 3,278,262 | 10/1966 | Poe et al. | 23/143 |
| 3,391,175 | 7/1968 | Davis | 260/448 |
| 3,391,219 | 7/1968 | Davis et al. | 260/683.15 |
| 3,394,990 | 7/1968 | Weingartner et al. | 568/840 |
| 3,647,374 | 3/1972 | Nomura et al. | 568/840 |
| 3,784,623 | 1/1974 | Motz | 260/677 R |
| 3,829,520 | 8/1974 | Ferrell | 260/677 |
| 3,886,264 | 5/1975 | Lindsay et al. | 568/840 |
| 3,887,691 | 6/1975 | Kobetz | 568/840 |
| 4,314,090 | 2/1982 | Shewbart et al. | 585/328 |
| 4,918,254 | 4/1990 | Diefenbach et al. | 585/328 |
| 4,935,569 | 6/1990 | Harkins et al. | 585/328 |

*Primary Examiner*—Werren B. Lone
*Attorney, Agent, or Firm*—David M. Bunnell

[57] ABSTRACT

This invention povides to a process for making an aluminum trialkyl product which process comprises reacting a mixture comprising, (i) an aluminum alkyl feed which contains one or more aluminum alkyls represented by the formula $R_3Al$, where R represents a $C_2$ to $C_{20}$ straight chain alkyl radical and each R can be the same or different, the alkyl radicals in said aluminum alkyl feed having an average chain length of at least about $C_8$, and (ii) a linear alpha-olefin feed which contains one or more linear alpha-olefins, said alpha-olefin feed having an average chain length which is at least about 2 carbons greater than the average chain length of the alkyl radicals in said aluminum alkyl feed, in the presence of a catalytic amount of a cobalt displacement catalyst, the reaction being at a temperature sufficient to displace olefins corresponding to R from said aluminum alkyl feed and to substitute in their place alkyl radicals derived from said linear alpha-olefin feed so as to form an aluminum trialkyl product having an average alkyl chain length which is greater than said aluminum alkyl feed, and the reaction being under sub-atmospheric pressure such that displaced olefins are removed form the reaction mixture. Long chain, linear alcohols can be prepared by oxidation and hydrolysis of the aluminum trialkyl products.

10 Claims, No Drawings

PREPARATION OF ORGANOALUMINUM COMPOUNDS AND LINEAR ALCOHOLS DERIVED THEREFROM

The invention relates generally to the preparation of long chain, linear alkyl aluminum and alcohol products by the ethylene chain growth process and more specifically to an improved process which utilizes a cobalt-catalyzed olefin displacement step.

Long chain, linear primary alcohols can be prepared by the oxidation and hydrolysis of aluminum alkyls in which one or more, and preferably, all of the alkyl groups contain 12 or more carbon atoms and, more preferably, 14 to 22 carbon atoms. In a typical example of such a process, an aluminum alkyl intermediate is formed by the chain growth reaction of ethylene with tri-ethylaluminum to produce a mixture of trialkylaluminum compounds having a Poisson distribution of alkyl chain lengths, for example of 2 to 20 carbon atoms, where the curve peaks at about $C_8$. This aluminum alkyl intermediate is then reacted with a mixture of alpha-olefins having a higher average carbon number than the aluminum alkyl intermediate in order to displace the alkyl groups and form an aluminum alkyl product which has an increased average alkyl chain length. Linear alcohols are then prepared by oxidation and hydrolysis of the aluminum alkyl product. A typical thermal displacement reaction requires temperatures of from about 340°-375° C. and is done in a closed system such that the displaced lighter olefins remain in the system. Because the displacement is a equilibrium reaction, the conversion of the aluminum alkyl intermediate to higher chain lengths is limited for example, to about 80 mole % when about a 350% excess of olefins is used and the aluminum alkyl product contains significant amounts of $C_2$ and $C_4$ alkyl groups. These lower alkyls will form ethanol and butanol upon oxidation and hydrolysis of the aluminum alkyl product, thus reducing the yield of the desired long chain linear alcohols. Also, some isomerization of the alpha-olefins to internal olefins occurs and branched alcohols arise from vinylidene olefins adding to aluminum alkyls during displacement.

U.S. Pat. No. 2,959,607 discloses the preparation of aluminum alkyls which contain at least one n-octyl group by subjecting octene-2 to the action of at least a stoichiometric amount of triisobutyl aluminum in the presence of a cobalt chloride catalyst at substantially atmospheric pressure. The catalyst apparently acts as both an isomerization and displacement catalyst in this process. The aluminum alkyls can be oxidized and hydrolyzed to make octanol-1.

U.S. Pat. No. 2,962,513 discloses a process for forming longer chain aluminum alkyls by a catalyzed olefin displacement of ethylene from ethyl aluminum compounds using a 100 to 300 percent stoichiometric excess of $C_3$ or higher alpha-olefins. The process uses salts and oxides of group VIII metal as catalysts at temperatures of from abut 50 to 200° C. at atmospheric pressure. Ethylene is evolved in the reaction.

U.S. Pat. No. 3,784,623 discloses the control of the increased tendency of the alpha-olefins to isomerize to internal olefins, which tendency is associated with catalytic displacement, by adding inhibitors or catalyst inactivators to the process.

We have now provided an efficient process that achieves catalytic displacement of aluminum alkyls at mild temperatures, while limiting the isomerization to internal olefins to only about 1-3 mole % of the alpha-olefin product without requiring the addition of isomerization inhibitors or catalyst inactivators to the displacement process. The higher aluminum alkyl products also contain less lighter alkyl and branched alkyl components compared to the thermal displacement process so that, when the aluminum alkyls are used to prepare long chain, linear, primary alcohols by oxidation and hydrolysis, the alcohol products will have improved purity.

In accordance with this invention there is provided a process for making an aluminum trialkyl product which process comprises reacting a mixture comprising, (i) an aluminum alkyl feed which contains one or more aluminum alkyls represented by the formula $R_3Al$, where R represents a $C_2$ to $C_{20}$ straight chain alkyl radical, and each R can be the same or different, the alkyl radicals in said aluminum alkyl feed having an average chain length of at least about $C_8$, and (ii) a linear alpha-olefin feed which contains one or more alpha-olefins, said alpha-olefin feed having an average chain length which is at least about 2 carbons greater than the average chain length of the alkyl radicals in said aluminum alkyl feed, in the presence of a catalytic amount of a cobalt displacement catalyst, the reaction being at a temperature sufficient to displace olefins corresponding to R from said aluminum alkyl feed and substitute in their place alkyl radicals derived from said linear alpha-olefin feed so as to form an aluminum trialkyl product having an average alkyl chain length which is greater than in said aluminum alkyl feed, and the reaction being under sub-atmospheric pressure such that displaced olefins are removed from the reaction mixture.

Also provided is a process for making linear alcohols which comprises the steps of: (a) reacting a mixture comprising, (i) an aluminum alkyl feed which contains one or more aluminum alkyls represented by the formula $R_3Al$, where R represents a $C_2$ to $C_{20}$ straight chain alkyl radical and each R can be the same or different, the alkyl radicals in said aluminum alkyl feed having an average chain length of at least about $C_8$, and (ii) a linear alpha-olefin feed which contains one or more linear alpha-olefins, said alpha olefin feed having an average chain length which is at least about 2 carbons greater than the average chain length of the alkyl radicals in said aluminum alkyl feed, in the presence of a catalytic amount of a cobalt displacement catalyst, the reaction being at a temperature sufficient to displace olefins corresponding to R from said aluminum alkyl feed and substitute in their place alkyl radicals derived from said linear alpha-olefin feed so as to form an aluminum trialkyl product having an average alkyl chain length which is greater than said aluminum alkyl feed, and the reaction being under sub-atmospheric pressure such that displaced olefins are removed from the reaction mixture, (b) oxidizing the aluminum trialkyl product and, (c) hydrolyzing the oxidized aluminum trialkyl product to form linear alcohols corresponding to the alkyl radicals in said aluminum trialkyl product.

The aluminum alkyl feed comprises one or more compounds represented by the formula $R_3Al$, where R represents $C_2$ to about $C_{20}$ straight chain alkyl radicals, which can be the same or different. The alkyl radicals in the aluminum alkyl preferably from about $C_8$ to $C_{12}$ and more preferably about $C_{10}$ with the amount of $C_2$ to $C_{10}$ material being at least about 60% by weight. The feed can be prepared by the well known Ziegler chain growth process in which a $C_2$-$C_4$ alpha olefin, and usually ethylene, is reacted with an aluminum alkyl such as triethylaluminum to produce an aluminum alkyl product in which the chain length of the alkyl groups have a Poisson, or pseudo Poisson distribution.

The preferred chain lengths for linear primary alcohols useful, for example, in making detergents are from about $C_{10}$ to $C_{18}$ and especially $C_{12}$ to $C_{14}$. When the chain growth process is operated to produce aluminum alkyl products having such chain lengths, a larger than desired amount of the less useful $C_{20+}$ heavy ends is also produced. Therefore, it is more efficient to produce the lower average chain length aluminum alkyl feed described above and then displace the lower alkyl groups using a molar excess of alpha-olefins having an average chain length of at least about 2 more carbons in order to form the heavier aluminum alkyl products from which the alcohols are prepared. For example, alpha-olefins having chain lengths of $C_{10}$ to about $C_{18}$. Such alpha-olefins can be obtained from the ethylene chain growth reaction on triethylaluminum, displacement of alkyl groups with lighter olefins, e.g. ethylene and/or butene, to provide a mixture of α-olefins, and then fractional distilla-tion to separate out the desired longer chain alpha-olefins. Particularly, useful feeds for making alcohols for detergents are mixtures of $C_{10}$ to $C_{18}$ alpha-olefins having an average chain length of about $C_{12}$ to $C_{14}$. A single carbon number $C_{10}$ to $C_{18}$ alpha-olefin feed can also be used for displacement.

In order to drive the equilibrium reaction to favor displacement of the lighter alkyls from the aluminum alkyls, at least about 10% and, preferably, at least about 50% up to a 1,000% stoichiometric excess of displacing olefins over the amount trialkylaluminum feed stream is used.

Suitable cobalt displacement catalysts include, but are not intended to be limited to cobalt acetylacetonate, and, preferably, cobalt carboxylates, i.e. cobalt naphthenate, cobalt acetate, cobalt tallate, cobalt (stearate), cobalt 2-ethyl-hexanoate, and the like. These catalysts, are effective to provide a displacement process at mild temperatures with surprisingly little (less than about 5 mol %) isomerization to internal olefins.

The catalyst is used in catalytic amounts, for example, from about 5 to 100 ppm and, preferably 10 to 50 ppm cobalt, based on the total weight of aluminum alkyl and olefin feed. Greater amounts can be used but increase the cost of the process.

The displacement reaction can be carried out at relatively mild temperatures of from about 50° to 150° C., and preferably from about 65° to 130° C. and at reduced pressure of from about 5 to 100 mm Hg so as to flash off the lighter, e.g. $C_2$ up to $C_{10}$ alpha-olefins during the displacement reaction to enhance the shift of the alkyl groups in the trialkyl aluminum product to the heavier $C_{12}$ to $C_{18}$ carbon numbers. This removal of displaced olefins also minimizes the amounts of ethyl and butyl groups and, consequently, the amounts of ethanol and butanol by-products in the alcohol product.

The process can be carried out in either a batch or continuous process and, preferably, in a flow-through, plug-flow reactor, for a sufficient time to provide the desired amount of conversion, e.g., at least about 50 mole percent and preferably from about 70 to 85 mol percent conversion of the alkyl groups in the aluminum alkyl feed based on $C_8$, while minimizing and side reactions such as isomerization of the alpha-olefins to internal olefins. Residence times of from about 1 to 45 minutes are generally satisfactory, and preferably 2 to 20 minutes.

The invention is further illustrated by, but is not intended to be limited to the following examples.

Example 1 is carried out in a continuous, two-stage displacement apparatus. Runs 1-14 were carried out in accordance with the following general procedure.

A mixture of tri-n-octylaluminum with about a 2-fold molar excess of 1-tetradecene ($C_{14}$) in a feed tank under nitrogen was continuously pumped at feed rates of about 2 to 100 cc/min. to an inlet tube of a heated, 3-neck first reactor equipped with a temperature indicator and a liquid vapor separation column which was connected to a water cooled condenser. A receiver and vacuum line were connected to the outlet end of the condenser. A selected amount of cobalt naphthenate catalyst (6% wt. in petroleum solvent) was pumped from a supply container into the reactant feed line to provide the selected catalyst concentrations of from 5 to 25 ppm cobalt, based on the total weight of reactant mixture. The first reactor was heated to temperatures of from about 220°-265° F. (105° to 30° C.) under a vacuum of about 30 to 65 mm Hg achieved by a first vacuum pump connected to the vacuum line which was equipped with a Zinelli gauge and a manometer. A portion of the n-octyl groups on the aluminum were displaced by n-tetradecyl groups and the resulting n-octene was removed through the column and condensed into the receiver. The partially displaced reaction mixture was removed through an outlet tube attached to the first reactor below the liquid level and feed to an inlet tube of a second reactor. The second reactor was equipped similarly to the first reactor except that the outlet tube was connected to a product receiving vessel. The second reactor was run at a pressure of about 11 mm Hg such that the transfer of reaction mixture to the second reactor was due to a pressure difference. Displaced 1-octene was again removed, condensed and collected. The residence times ranged from about 1 to 5 minutes (preferably 1-2 min.) in the first reactor and 5 to 20 minutes (preferably 4-6 min.) in the second stage. Portions of the reaction mixture from the first stage and the product were analyzed to determine the percent displacement and the amount of impurities. The process parameters and the results for runs 1-14 are tabulated in Table I below in which the percentages are molar.

TABLE I

| | | | | | | | | | | | Heavy |
|---|---|---|---|---|---|---|---|---|---|---|---|
| | | Feed | Pres. | | | | % | | | | End % |
| | ppm | Rate | mm Hg | | Temp °F. | | Displacement | | % Vinyl | % Branched | |
| Run | Co | cc/mn | 1st | 2nd | 1st | 2nd | 1st | 2nd | Isomerized | Alkyl | C_ |
| 1 | 5 | 2.4 | 65 | 11 | 265 | 170 | 6.3 | 7.3 | — | — | — |
| 2 | 15 | 5.6 | 40 | 11 | 260 | 180 | 79.7 | 86.7 | 4.2 | — | — |
| 3 | 10 | 4.6 | 31 | 11 | 260 | 170 | 61.7 | 64.1 | 1.8 | 2.2 | — |
| 4 | 25 | 4.6 | 35 | 11 | 235 | 170 | 87.0 | 87.0 | 11.0 | 2.1 | 1.2 |
| 5 | 25 | 4.6 | 35 | 11 | 235 | 170 | 75.0 | 83.0 | 6.6 | 1.76 | 2.1 |
| 6 | 15 | 4.6 | 35 | 11 | 235 | 170 | 80.0 | 87.0 | 5.6 | 1.8 | 0.7 |

TABLE I-continued

CATALYTIC DISPLACEMENT 2-STAGE RUNS

| Run | ppm Co | Feed Rate cc/mn[1] | Pres. mm Hg 1st | Pres. mm Hg 2nd | Temp °F. 1st | Temp °F. 2nd | % Displacement 1st | % Displacement 2nd | % Vinyl Isomerized | % Branched Alkyl | Heavy End % C_ |
|---|---|---|---|---|---|---|---|---|---|---|---|
| 7 | 10 | 4.6 | 35 | 11 | 235 | 170 | 86.0 | 86.0 | 4.3 | 2.0 | — |
| 8 | 15 | 4.6 | 35 | 11 | 220 | 170 | 82.0 | 90.0 | 4.6 | 1.8 | 0.38 |
| 9 | 15 | 4.6 | 35 | 11 | 220 | 150 | 77.4 | 85.5 | 4.6 | 1.7 | 1.2 |
| 10 | 10 | 4.6 | 35 | 11 | 220 | 150 | 71.0 | 76.5 | 2.8 | 1.7 | 1.3 |
| 11 | 10 | 8.6 | 35 | 11 | 220 | 150 | 62.0 | — | — | 2.0 | 2.3 |
| 12 | 10 | 8.6 | 35 | 11 | 220 | 150 | 73.0 | 75.0 | — | 1.8 | — |
| 13 | 10 | 10.0 | 35 | 11 | 220 | 150 | — | 76.0 | — | 1.6 | — |
| 14 | 10 | | 40 | 11 | 230 | 170 | | | | | |

[1]Feed Rate

In contrast to the cobalt catalyzed runs which achieved up to 90% displacement with less than 5% isomerization to internal olefins in run 8, nickel-catalyzed displacements caused 30–60% isomerization to internal olefins.

The product $C_{14}$ aluminum alkyls can be converted to alcohols by the process of oxidation and hydrolysis. We have found that the residual cobalt catalyst need not be removed from the alkyl aluminum product prior to its conversion to alcohols. In fact average oxidation rates have been observed to increase.

The oxidation apparatus consists of a one-liter Parr reactor and pump-around loop for cooling and gas/liquid separation. Air or nitrogen can be fed to the reactor through rotameters into a dip tube below the agitator. Aluminum alkyl is fed from a tank through a rotameter into the recirculation loop. In operation, a liquid/gas mixture is transferred from the reactor to a K.O. pot where the gas (nitrogen) is separated and vented to an oxygen analyzer. The liquid is then pumped through a cooler and rotameter and then back to the reactor. Liquid product is removed from the unit at the same rate as the feed.

In the first oxidation step, aluminum alkyl is continuously fed and product removed from the system. In the second oxidation step, no aluminum alkyl is fed or removed and the system operates in a batch mode. The operating procedure for each step is as follows:

First Oxidation

1. Fill feed tank with alkyl/olefin mixture.
2. Pump about one liter of feed into the reactor and start gear pump to circulate liquid from the K.O. pot through the cooler and back to the autoclave.
3. Batch oxidize with air for 20–25 minutes to bring oxidation to 60–65 percent. Maintain reactor pressure at 40 psig.
4. Start aluminum alkyl feed at about 40 g/min and begin product withdrawal at same rate. Maintain temperature at 115°–150° F.
5. After about two liters of product has been collected, sample product and stop air and aluminum alkyl feed.

Second Oxidation

1. Vent the pressure off the reactor and add a weighed amount of TiCl$_4$ catalyst.
2. Pressure the reactor to 40 psig, start recirculation loop and heat to 120° F.
3. Begin air feed and slowly raise the temperature to 160° F.
4. When $O_2$ in the vent reaches 8%, begin soak period by cofeeding nitrogen to maintain 8% $O_2$ in the vent.
5. Continue soak period for 2 hours and then cool and remove product.

The product from second oxidation is fed to a Pope wiped-film still which removes the solvent and hydrocarbon impurities from the alkoxide with the bottoms temperature held at a minimum of 450° F. at 5 mm Hg vacuum.

The presence of 5 ppm cobalt in second oxidation was observed to increase the oxidation rate at least 25% and the yield slightly (95–97% vs normal 93–95%). Some increase in free alcohol was noted during alkoxide stripping. Upon acid hydrolysis all of the cobalt was recovered with the alum as was the case with the following simulation. Washing and distillation of the crude alcohol product provided alcohol fractions which were within specifications. It is expected that free alcohol production during oxidation can be minimized by reducing or eliminating the soak period.

According to the hydrolysis process, the product alkoxide Al(OR)$_3$ from the wiped-film still is reacted in a circulation loop with sulfuric acid to produce crude alcohol and alum, Al$_2$(SO$_4$)$_3$. The product mixture is two-phase and the alum is separated from the mixture. The crude alcohol is then passed through an acid wash, a caustic wash and two water washes.

A normal alkoxide feed to which 20 ppm cobalt had been added in order to simulate the presence of residual catalyst was hydrolyzed. The cobalt did not change the process compared to cobalt-free hydrolysis and all of the added cobalt appeared in the alum.

What is claimed is:

1. A process for making linear alcohols which comprises the steps of: (a) reacting a mixture comprising, (i) an aluminum alkyl feed which contains one or more aluminum alkyls represented by the formula R$_3$Al, where R represents a C$_2$ to C$_{20}$ straight chain alkyl radical and each R can be the same or different, the alkyl radicals in said aluminum alkyl feed having an average chain length of at least about C$_8$, and (ii) a linear alpha-olefin feed which contains one or more linear alpha-olefins, said alpha-olefin feed having an average chain length which is at least about 2 carbons greater than the average chain length of the alkyl radicals in said aluminum alkyl feed, in the presence of a catalytic amount of from about 5 to 100 ppm based on the total weight of aluminum alkyl feed and linear alpha-olefin feed of a cobalt displacement catalyst, the reaction being at a temperature of from about 50° to 150° C. which is sufficient to displace olefins corresponding to R from said aluminum alkyl feed and to substitute in their place alkyl radicals derived from said linear alpha-olefin feed so as to form an aluminum trialkyl product having an average alkyl chain length which is greater than said aluminum alkyl feed, and the reaction being under sub-atmospheric pressure of from about 5 to 100 mm Hg such that displaced olefins are removed from the reaction mixture, (b) oxidizing the aluminum trialkyl product formed in the reaction mixture, and then (c) hydrolyzing the oxidized aluminum trialkyl product to form linear alcohols corresponding to the alkyl radicals from said aluminum trialkyl product.

2. A process according to claim 1 wherein the alkyl radicals in said aluminum alkyl feed have an average chain length of from about $C_8$ to $C_{12}$, said linear alpha-olefin feed has an average chain length of from about $C_{12}$ to $C_{14}$ and displaced olefins of up to $C_{10}$ are removed from said reaction mixture.

3. The process according to claim 2 wherein the aluminum alkyl feed comprises a mixture of aluminum alkyls and said linear alpha-olefin feed comprises a mixture of alpha-olefins having chain lengths of from about $C_{10}$ to $C_{18}$.

4. The process according to claim 3 wherein the aluminum alkyl feed has an average chain length of about $C_{10}$ with the amount of $C_2$ to $C_{10}$ alkyl radicals in said aluminum alkyl feed being about 60% by weight of the total amount of alkyl radicals therein.

5. The process according to claim 1 wherein said cobalt catalyst is selected from cobalt acetylacetonate and cobalt carboxylates.

6. The process according to claim 5 wherein the aluminum alkyl feed comprises a mixture of aluminum alkyls wherein the alkyl radicals have an average chain length of from about $C_8$ to $C_{12}$ and the linear alpha-olefin feed comprises a mixture of alpha-olefins having chain lengths of from about $C_{10}$ to $C_{18}$ and an average chain length of from about $C_{12}$ to $C_{14}$.

7. The process according to claim 6 wherein at least about a 50% stoichiometric excess of linear alpha-olefin feed over the amount of aluminum alkyl feed is used in the reaction and at least about 50 mol percent of the alkyl radicals in said aluminum alkyl feed are displaced by linear alpha-olefin.

8. The process according to claim 7 wherein at least about 70 mol percent of the alkyl radicals are displaced by linear alpha-olefin.

9. The process according to claim 1 wherein said cobalt catalyst is present in step (b) and acts to increase the oxidation rate of said aluminum trialkyl product.

10. The process according to claim 1 wherein the oxidizing in step (b) is carried out in the presence of oxygen as the oxidizing agent and the hydrolyzing in step (c) is carried out in the presence of an acid hydrolyzing agent.

* * * * *